United States Patent [19]
Bourne et al.

[11] Patent Number: 5,911,720
[45] Date of Patent: Jun. 15, 1999

[54] ABLATION CATHETER WITH SEGMENTED TIP

[75] Inventors: Thomas M. Bourne, Mountain View; David McGee, Sunnyvale; Thomas F. Kordis, San Jose, all of Calif.

[73] Assignee: EP Technologies, Inc., Sunnyvale, Calif.

[21] Appl. No.: 08/756,721

[22] Filed: Nov. 26, 1996

[51] Int. Cl.⁶ ................................................. A61B 17/36
[52] U.S. Cl. ............................ 606/41; 600/374; 607/122
[58] Field of Search .......................... 606/41, 42, 45–52; 607/122; 600/372–374

[56] References Cited

U.S. PATENT DOCUMENTS

| | | | |
|---|---|---|---|
| 5,125,925 | 6/1992 | Parins et al. | 606/48 |
| 5,133,365 | 7/1992 | Heil, Jr. et al. | 607/122 |
| 5,411,025 | 5/1995 | Webster, Jr. | 607/122 |
| 5,429,131 | 7/1995 | Scheinman et al. | 607/122 |
| 5,462,545 | 10/1995 | Wang et al. | 606/41 |
| 5,536,267 | 7/1996 | Edwards et al. | 606/41 |
| 5,549,108 | 8/1996 | Edwards et al. | 607/122 |
| 5,617,854 | 4/1997 | Munsif | 606/50 |
| 5,680,860 | 10/1997 | Imran | 600/374 |

*Primary Examiner*—Michael Peffley
*Attorney, Agent, or Firm*—Lyon & Lyon LLP

[57] ABSTRACT

An ablation catheter having self assembling large surface area distal component provided with one or more energy emitting surfaces for thermally destroying tissue. The distal component is oriented to present a compact, low profile for introduction into the heart, and after introduction is reconfigured to present a large surface area distal ablation tip assembly. The distal tip component is subsequently returned to the low profile configuration for removal from the heart. Once introduced, the energy emitting surfaces are thus carried by a distal component having significantly enlarged surface area. The enlargable distal component is produced using a plurality of pivoting sections capable of alignment into a compact profile for introduction into and removal from a living body. When reconfigured by pivoting of the sections into contact with each other, the distal component has an significantly enlarged dimension.

19 Claims, 4 Drawing Sheets

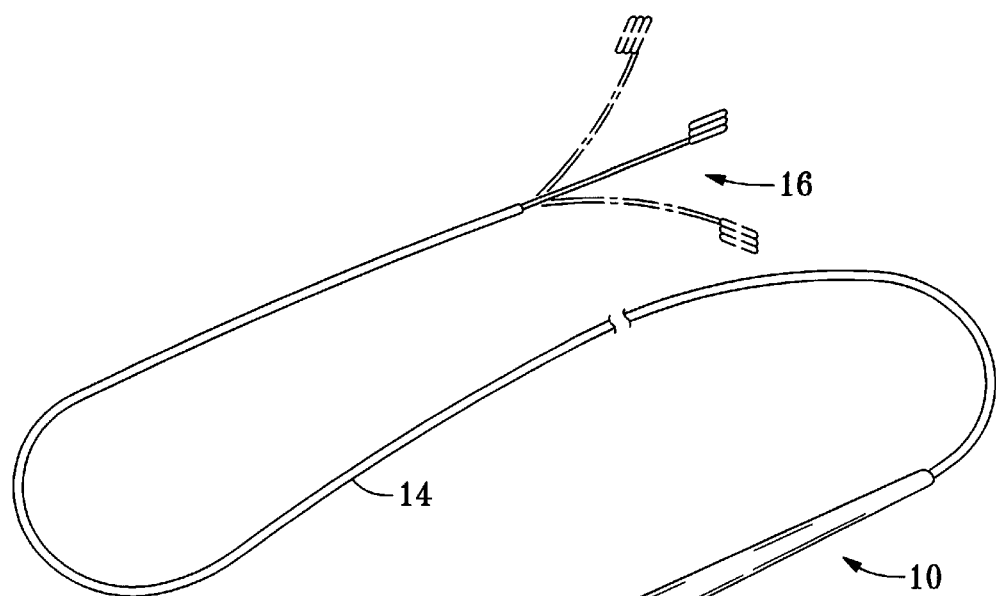
*fig.1*
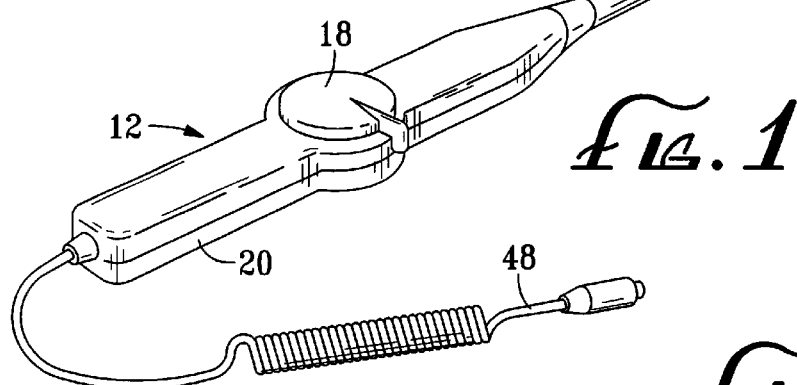
*fig.2*
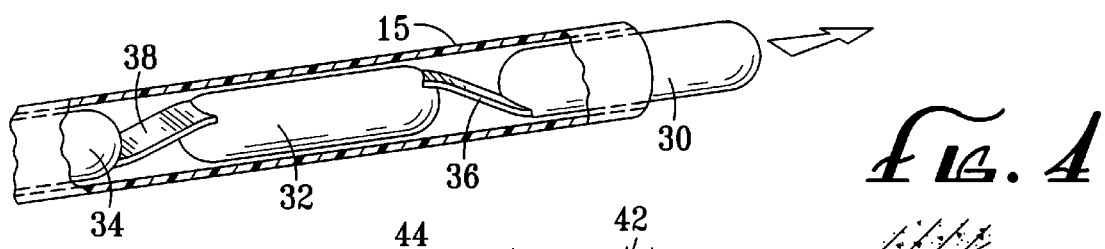
*fig.4*
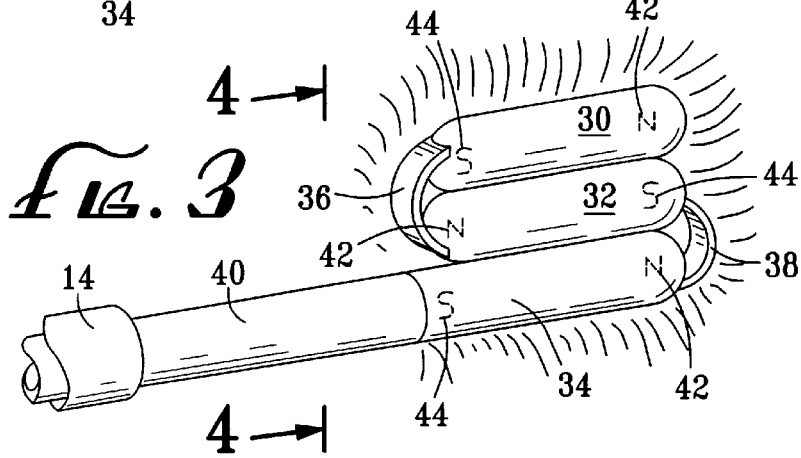
*fig.3*
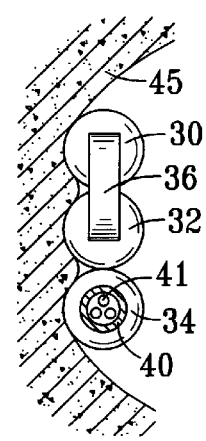

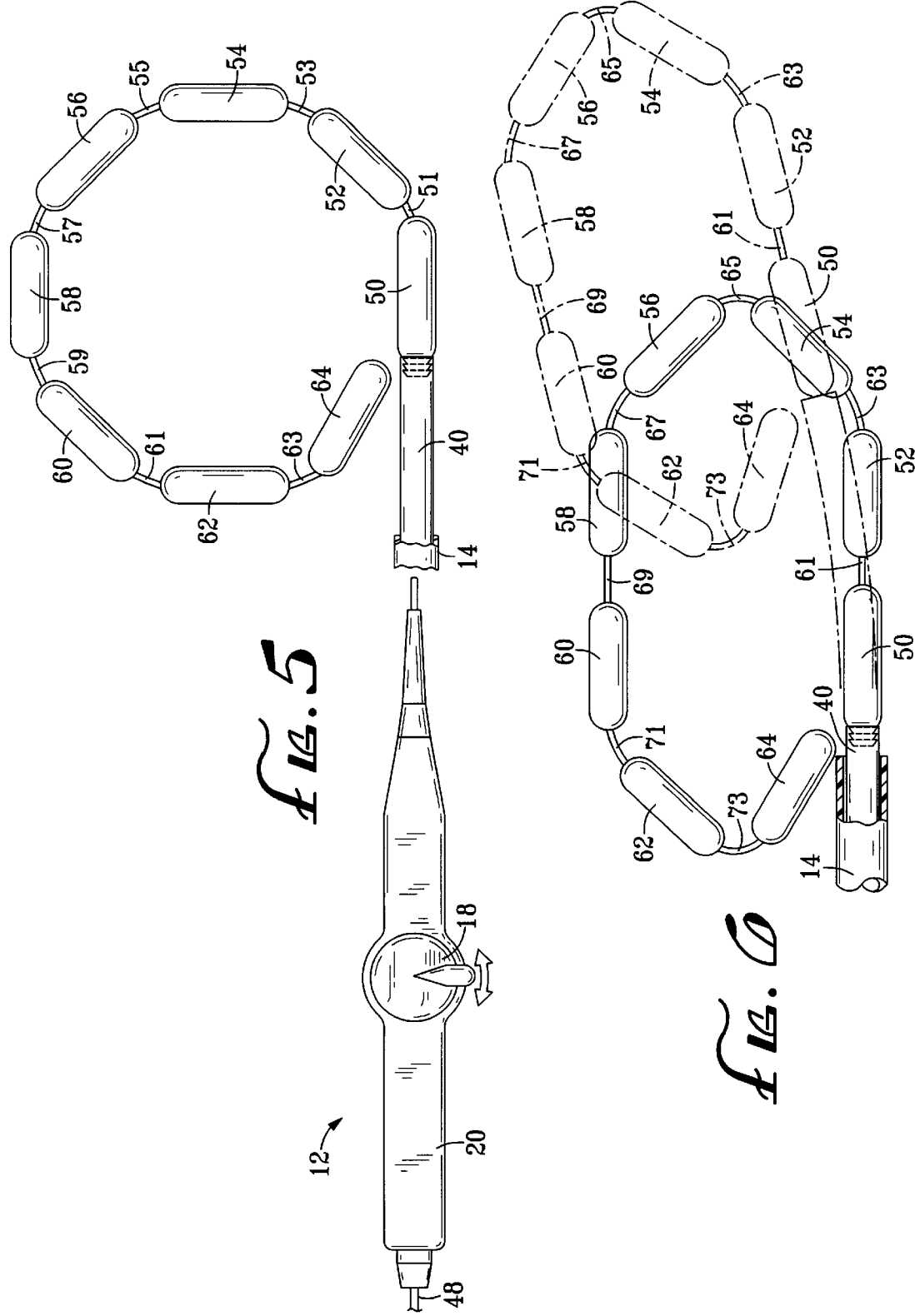

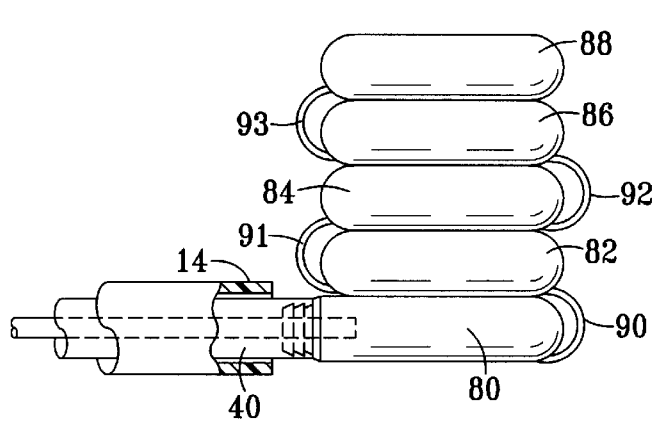
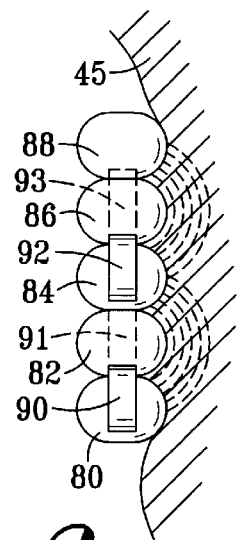
fig. 7          fig. 8
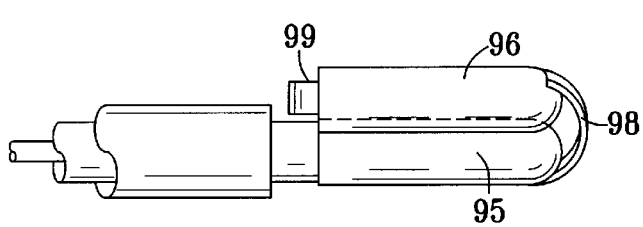
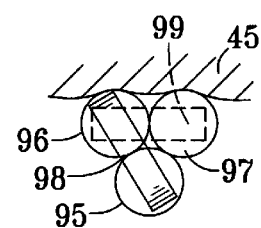
fig. 9          fig. 10

ABLATION CATHETER WITH SEGMENTED TIP

FIELD OF THE INVENTION

This invention relates to catheters having a distal tip assembly that has a low profile for introduction into the body and which can be enlarged within a body cavity for use in performing medical procedures. More specifically, the invention provides systems and methods applicable for ablating the interior regions of the heart for treating cardiac conditions.

BACKGROUND OF THE INVENTION

It is believed that lesions larger than those created by current electrophysiological therapy are needed to more consistently cure monomorphic ventricular tachycardia (MVT) of ischemic origins.

Conventional cardiac ablation systems designed to cure re-entrant supraventricular tachycardia (SVT), often create lesions in myocardial tissue with a penetration depth of about 3 to 5 mm and a lesion volume of less than 0.2 cm$^3$, depending upon the size of the electrode and the amount of power that is applied.

However, to consistently cure MVT by ablation, a penetration depth greater than 3 to 5 mm and a lesion volume of at least 1 cm$^3$ is estimated to be required.

The solution lies in larger electrodes. Yet, larger electrodes themselves pose problems of size and maneuverability that weigh against safe and easy introduction through a vein or artery into the heart.

A need exists for cardiac ablation catheters having that flexibility and maneuverability that permits safe and easy introduction into the heart and, once deployed inside the heart, emit energy sufficient to cause permanent, irreversible thermal damage to large regions of myocardial tissue.

SUMMARY OF THE INVENTION

The invention provides an ablation catheter having large surface area distal component provided with one or more energy emitting surfaces for thermally destroying tissue. The distal component is oriented to present a compact, low profile for introduction into the heart, and after introduction is reconfigured to present a large surface area distal ablation tip assembly. The distal tip component is subsequently returned to the low profile configuration for removal from the heart.

Once introduced, the energy emitting surfaces are thus carried by a distal component having significantly enlarged mass. The invention thus provides catheters capable of emitting ablation energy sufficient to create a lesion that is significantly larger in terms of volume and geometry than the surface's initial low profile would provide.

The catheter of this invention is configured to produce lesions with a greater surface area, compared to standard cardiac ablation catheters, while maintaining a small (4 to 8 French) introducer size (Note that one "French" equals ⅓ mm or approximately 0.013 inches).

The large effective size of the electrodes creates larger lesions, because the shape and size of the energy emitting surface are factors which control the lesion volume and geometry.

In accordance with a further aspect of the invention, an enlargable distal component is produced using a plurality of pivoting sections capable of alignment into a compact profile for introduction into and removal from a living body. The sections carry ablation electrodes. When reconfigured by pivoting of the sections into contact with each other, the distal component has a significantly enlarged dimension of, for example, approximately 12 to 20 French.

Another aspect of the invention is relates to the use of springs to connect the pivoting sections. The springs bias the assembly to the expanded position while the sections are retained in the compact profile position within a guide catheter during introduction and withdrawal from the body cavity.

In an optional arrangement, the distal component can also be provided with mapping electrodes for obtaining electrogram recordings or for completing similar mapping procedures in addition to performing as ablation electrodes.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

BRIEF DESCRIPTION OF DRAWINGS

FIGS. 1 is an isometric view showing an embodiment of an ablation catheter system, with the distal tip assembly shown in alternative positions by means of phantom lines;

FIG. 2 is a greatly magnified broken-away view of a distal tip assembly, in accordance with the invention, with the tip assembly retracted into the guiding catheter;

FIG. 3 is a fragmentary view of the assembly of FIG. 2 with the distal tip assembly extended beyond the distal end of the guiding catheter;

FIG. 4 is a sectional view taken along line 4—4 and further illustrating the distal tip component in contact with myocardial tissue;

FIG. 5 is a fragmentary top plan view with parts magnified and in section showing an alternative embodiment of the invention and with an alternative position of the components shown by phantom lines;

FIG. 6 is a fragmentary magnified top plan view of a distal tip assembly illustrating yet another embodiment of the invention;

FIG. 7 is a fragmentary magnified top plan view of a distal tip assembly illustrating another embodiment of the invention;

FIG. 8 is an end view of the catheter of FIG. 7 shown in contact with myocardial tissue.

FIGS. 9 and 10 are fragmentary side and end views, respectively, of a distal tip assembly illustrating yet another embodiment of the invention.

DESCRIPTION OF PREFERRED EMBODIMENTS

Figure 11:
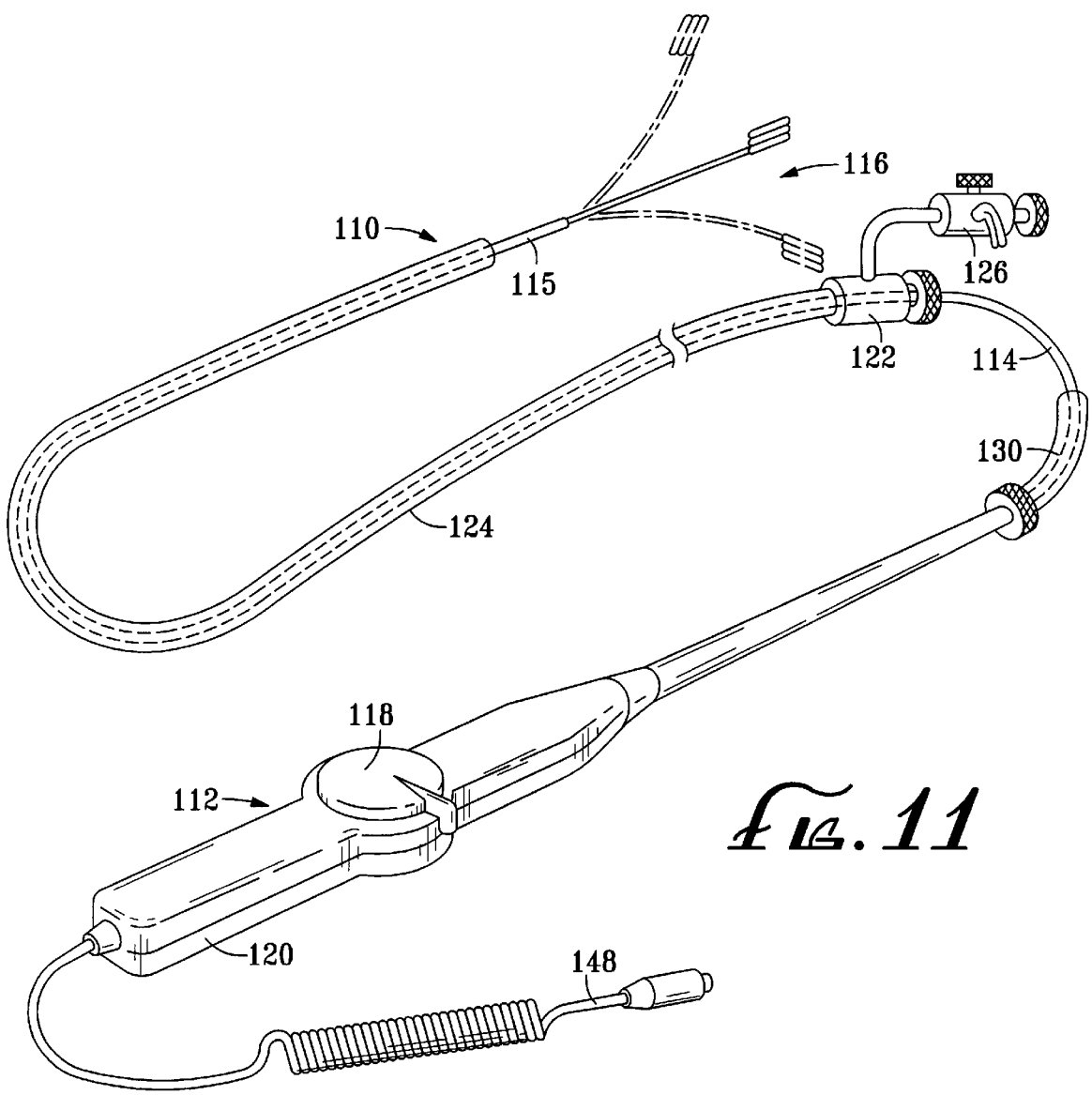
FIG. 11 is an isometric view similar to FIG. 1 showing an alternative embodiment of a ablation catheter system used in connection with the present invention, with the distal tip assembly shown in alternative positions by means of phantom lines.

FIG. 1 shows a steerable catheter 10 that embodies the features of the invention. As there shown, the catheter 10 includes three main parts or assemblies: the handle assembly 12, the guide tube assembly 14, and the electrode tip assembly 16. An electrical cable 48 for providing power to an electrode at the distal tip of the catheter attaches to the back of the housing 20.

The catheter 10 can be used in a number of different environments and in various body cavities or organs. This specification will describe the catheter 10 as used to provide electrophysiologic therapy in the interior regions of the heart.

An alternative embodiment 110 of a catheter system useable in conjunction with the invention is shown in FIG. 11. As there shown, the catheter 110 includes three main parts or assemblies: the handle assembly 112, the guide tube assembly 114, and the electrode tip assembly 116. An electrical cable 148 for providing power to an electrode at the distal tip of the catheter attaches to the back of the housing 120. A hemostat 122 is attached to the proximal end of introducing guide sheath 124. A stopcock and flush port 126 are also connected to hemostat 122. A tip sheath 130 is provided to facilitate introduction of the catheter 110 through hemostat 122, after which it is withdrawn to the position illustrated in FIG. 11.

When using catheter 110, a physician may first place a guiding catheter 124 into the appropriate chamber of the heart assisted by the use of a guide wire and pigtail catheter. After removal of the pigtail and guide wire, the multiple electrode elements of the preferred embodiment are straightened by introduction into a short section of tubing 130 of the same diameter as the guiding catheter 124. This tubing 130 serves the dual function of straightening out the multiple segments in preparation for introduction and to allow the penetration of the assembly through the hemostat valve 122 that is characteristically employed on the proximal end of the guide catheter 124.

The physician then pushes the ablation catheter assembly 110 through the guiding catheter 124 until it emerges from the distal end of the guiding catheter 124, those segments self-assemble into the large distal ablation tip shown in FIGS. 3 through 10.

Once the ablation tip segments have fully emerged along with a length of the catheter body, the physician can use the handle assembly 12 or 112. When used for this purpose, a physician grips the handle assembly 12 or 112 to steer the guide tube assembly 14 or 114 through a main vein or artery (which is typically the femoral vein or artery) into the interior region of the heart that is to be treated. The physician then further manipulates a steering mechanism 18 or 118 on the handle assembly 112 (which will be described later) to place the electrode tip assembly 116 in contact with the tissue that is to be ablated. The physician directs radio frequency energy into the electrode tip assembly 16 or 116 to ablate the tissue contacting the electrode tip assembly 16/116.

Further details of various steering assemblies are more fully described in commonly owned U.S. Pat. Nos. 5,273,535, 5,254,088, and 5,358,478, the disclosures of which are herein incorporated by reference.

The distal tip portion 16/116 of the catheter assembly 14/114 is shown in greater detail in FIGS. 2–10 which include various alternative embodiments. In the embodiment shown in FIGS. 2–4 a distal tip assembly includes three segments 30, 32, and 34, which are pivotable relative to each other. Segments 30 and 32 are connected by a means of a flattened spring 36 and sections 32 and 34 are connected by a similar flattened spring 38. The springs provide a biasing force to cause the segments to pivot from the configuration of FIG. 2 which provides the distal tip assembly a profile no larger than the diameter of the catheter body 14/114 to a second configuration shown in FIG. 3 wherein the assembly has a substantially larger dimension. Spring segments 36 and 38 can be formed from stainless steel, nitinol or various other suitable metal alloys having resilient characteristics. Preferably the spring segments 36 and 38 are electrically insulated so that they do not act as electrodes.

Each segment 30, 32, and 34 may consist of an electrode such as a platinum-iridium electrode element. As also seen in FIG. 3 the assembly is carried by a hollow shaft or stylet 40 within which electrically conductors 41 are contained. Hollow shaft 40 is of a sufficient strength to enable support and manipulation of the electrode tip assembly and also to facilitate retracting the same into the distal end of guide catheter 14/114 after the conclusion of the ablation procedure, to thereby enable retraction of the assembly from the heart chamber. As seen in FIG. 4 the assembly enables contact of ablation electrodes with a significantly greater area of the myocardial tissue 45 than would be possible with a catheter tip having a diameter substantially equal to the diameter of guide catheter 14.

A magnet can also be positioned within each of the sections 30, 32, and 34. Such magnets will assist placement of the electrode sections into proper orientation relative to each other. In this case the magnets are oriented with the polarity of every other magnet reversed so that the north pole 42 of will be in alignment with the south pole 44 of an adjoining magnet. By use of this optional feature orientation of the tip into a compact predetermined configuration to create an effective ablation tip two to six times the diameter of the individual sections is assisted.

In the embodiments of FIGS. 5 and 6 different alternative shapes for the distal tip assembly are disclosed. Referring to FIG. 5 there is a series of electrode elements 50, 52, 54, 56, 58, 60, 62, and 64. These segments are connected by a series of springs 51, 53, 55, 57, 59, 61, and 63 as shown. The springs bias the series of segments into a generally octagonal structure which is capable of placement in contact with a substantial area of the myocardial tissue. Each of the springs 51, etc. is preshaped so that the assembly will be biased into the configuration of FIG. 5 when the distal tip assembly is extended distally from the guide catheter body 14.

In the arrangement of FIG. 6 the electrode segments 50, 52, 54, 56, 58, 60, 62, and 64 are interconnected by means of flat springs 60, 63, 65, 67, 69, 71, and 73 which have a different preshaped bias, so that an elongated octagon, as seen in FIG. 6, is formed when the segments are released from within the body of guide catheter 14.

Preferably, a steering mechanism, of the type described in the foregoing patents incorporated by reference, is included in the distal end tube 40. This enables bending of the distal tip assembly and accurate placement to a desired site within the heart.

Such steering is illustrated, for example, by the phantom lines shown in FIG. 5. Even greater bending capacity can be provided as desired.

In the further embodiment of FIGS. 7 and 8, a series of five electrode segments 80, 82, 84, 86, and 88 are provided. These segments are interconnected by means of spring segments 90–93, as shown. In FIG. 8 it will be noted that the adjoining lateral surfaces between segments 80–88 are flattened so that they will fit relatively compactly against each other. A greater degree of flattening than shown may be utilized, if desired. Also, other mating configurations, ie., interlocking, or tongue and groove, etc. can be utilized, if desired.

In the embodiments of FIGS. 9 and 10 another alternative configuration for the distal tip assembly is disclosed. Referring to FIG. 9 there is are three electrode elements 95, 96 and 97. These segments are connected by springs 51, 98 and 99 as shown. The springs 98 and 99 bias the series of segments into a generally triangular arrangement, as shown, which is capable of placement in contact with a larger area of the myocardial tissue than would be possible using a single electrode element. Each of the springs 98 and 99 etc. is preshaped so that the assembly will be biased into the configuration of FIGS. 9 and 10 when the distal tip assembly is extended distally from the guide catheter body 14/114.

While various preferred embodiments of the invention have been shown for purposes of illustration it will be understood that those skilled in the art may make modifications thereof without departing from the true scope of the invention as set forth in the appended claims including equivalents thereof.

What is claimed is:

1. A catheter, comprising:
    an elongate catheter body adapted to be movably disposed in a guide sheath; and
    an electrode assembly operatively connected to a distal end of the catheter body, the electrode assembly comprising a plurality of successively connected sections laterally pivotable relative to each other and adapted to be carried in longitudinal succession relative to the catheter body when disposed in a guide sheath.

2. A catheter according to claim 1, further comprising a temperature sensing electrode operatively connected to the catheter body.

3. A catheter according to claim 1, wherein the sections are connected to each other by means configured to position the respective sections into contact with one another when the electrode assembly is extended through an opening of the guide sheath.

4. A catheter according to claim 3, wherein each of the sections has a lateral surface in contact with a lateral surface of an adjoining section when the electrode assembly is extended beyond the guide sheath opening, the respective contacting surfaces flattened so as to fit relatively compactly against each other.

5. A catheter according to claim 1, wherein at least one electrode is carried by each section.

6. A catheter according to claim 1, wherein each of the plurality of successively connected sections has at least one adjoining section, and
    wherein the respective adjoining sections are connected to each other by means of flattened preformed springs.

7. A catheter according to claim 6, wherein each spring is electrically insulated.

8. A catheter according to claim 1, wherein each section comprises a platinum iridium electrode element.

9. A catheter according to claim 1, further comprising a conductor electrically coupled to one or more electrodes carried by the electrode assembly.

10. A catheter according to claim 9, each section comprising a magnet arranged with its polarity opposite that of each respective adjoining section, whereby alignment of the adjoining sections relative to each other is thereby maintained.

11. A catheter assembly, comprising:
    an elongate catheter body having a longitudinal axis and adapted to be movably disposed in a guide sheath; and
    an electrode assembly operatively connected to a distal end of the catheter body, the electrode assembly comprising a plurality of successively connected sections laterally pivotable relative to each other and adapted to be carried in longitudinal succession relative to the catheter body when disposed in a guide sheath,
    wherein the sections are interconnected by means configured to position the respective sections into contact with one another when the electrode assembly is extended through an opening of a guide sheath, each section having at least one adjoining section, and
    wherein the adjoining sections are connected to each other by respective flattened preformed springs, which bias the respective sections when the electrode assembly is extended beyond an opening of a guide sheath.

12. A catheter according to claim 11, further comprising at least one sensing electrode operatively connected to the catheter body.

13. A catheter according to claim 11, each section comprising a magnet arranged with its polarity opposite that of each respective adjoining section, whereby alignment of the adjoining sections relative to each other is maintained.

14. A catheter according to claim 11, wherein each of the sections has a lateral surface in contact with a lateral surface of an adjoining section when the electrode assembly is extended beyond the guide sheath opening, the respective contacting surfaces flattened so as to fit relatively compactly against each other.

15. A catheter according to claim 11, further including steering means operatively connected to the catheter body.

16. A catheter according to claim 11, wherein at least one electrode is carried by each section.

17. A catheter according to claim 16, wherein each electrode comprises platinum iridium.

18. A catheter according to claim 11, wherein each spring is electrically insulated.

19. A catheter according to claim 11, further comprising a conductor electrically coupled to one or more electrodes carried by the electrode assembly.

* * * * *